(12) United States Patent
Matsumoto et al.

(10) Patent No.: US 9,541,493 B2
(45) Date of Patent: Jan. 10, 2017

(54) INSPECTION APPARATUS USING POLARIZED LIGHTS

(71) Applicant: YOKOGAWA ELECTRIC CORPORATION, Tokyo (JP)

(72) Inventors: Yoshinori Matsumoto, Tokyo (JP); Takashi Tsubota, Tokyo (JP); Toyoaki Hamaguchi, Tokyo (JP); Akishige Ito, Tokyo (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 39 days.

(21) Appl. No.: 14/724,932

(22) Filed: May 29, 2015

(65) Prior Publication Data

US 2015/0346083 A1    Dec. 3, 2015

(30) Foreign Application Priority Data

Jun. 2, 2014   (JP) .................. 2014-113950

(51) Int. Cl.
*G01N 21/21* (2006.01)
*G01N 21/84* (2006.01)
(Continued)

(52) U.S. Cl.
CPC .......... *G01N 21/21* (2013.01); *G01N 21/8422* (2013.01); *G01N 21/8851* (2013.01);
(Continued)

(58) Field of Classification Search
CPC ................. G01N 2021/8848; G01N 2021/213; G01N 2021/4792; G01N 2021/8845; G01N 21/21; G01N 21/8422; G01N 21/8851; G01N 21/8901; G01N 21/25; G01N 21/88; G01N 21/9501; G01N 21/9506; G01N 2201/0612; G01N 2201/062
See application file for complete search history.

(56) References Cited

U.S. PATENT DOCUMENTS 4,893,932 A    1/1990  Knollenberg
5,081,348 A *  1/1992  Siddiqui ................. G01J 4/04
                                                    250/225
(Continued)

FOREIGN PATENT DOCUMENTS

JP       9-178666 A    7/1997
JP    2007-322316 A   12/2007
JP     2012-68270 A    4/2012

*Primary Examiner* — Gordon J Stock, Jr.
(74) *Attorney, Agent, or Firm* — Sughrue Mion, PLLC (57) ABSTRACT

An inspection apparatus using polarized lights according to one aspect of the present invention includes an irradiator configured to irradiate an inspection target with a first plurality of lights. The first plurality of lights have different polarization states and different wavelengths from each other. The inspection apparatus further includes a light receiver configured to perform a wavelength demultiplexing of a second plurality of lights obtained from the inspection target to generate a third plurality of lights, to separately receive the third plurality of lights, and to output at least one light-receiving signal associated with the third plurality of lights and a processor configured to calculate at least one of an ellipse azimuth, a degree of polarization, and a polarization component intensity using the light-receiving signal and to determine whether the inspection target is defective or non-defective.

20 Claims, 8 Drawing Sheets

(51) Int. Cl.
  *G01N 21/89*  (2006.01)
  *G01N 21/88*  (2006.01)
(52) U.S. Cl.
  CPC . *G01N 21/8901* (2013.01); *G01N 2021/8848* (2013.01); *G01N 2201/062* (2013.01); *G01N 2201/0612* (2013.01)

(56) References Cited

U.S. PATENT DOCUMENTS

| | | | | |
|---|---|---|---|---|
| 5,202,744 | A * | 4/1993 | Louis | G01N 21/6408 356/417 |
| 5,440,390 | A * | 8/1995 | Tirri | G01J 4/04 356/364 |
| 5,910,841 | A | 6/1999 | Masao | |
| 7,285,767 | B2 | 10/2007 | Harding | |
| 2002/0044282 | A1* | 4/2002 | Moeller | G01J 3/447 356/369 |
| 2005/0029469 | A1* | 2/2005 | Schroder | A24C 5/3412 250/458.1 |
| 2005/0041249 | A1* | 2/2005 | Dobbs | G01J 3/447 356/364 |
| 2006/0279741 | A1* | 12/2006 | Hirata | H04J 14/06 356/491 |
| 2007/0121105 | A1* | 5/2007 | Yoo | G01B 11/2513 356/237.2 |
| 2012/0080611 | A1* | 4/2012 | Jones | G01J 1/0242 250/458.1 |
| 2013/0050701 | A1* | 2/2013 | Jensen | G01B 11/007 356/369 |
| 2013/0235374 | A1* | 9/2013 | Biellak | G01N 21/9501 356/237.5 |

* cited by examiner

INSPECTION APPARATUS USING POLARIZED LIGHTS

BACKGROUND OF THE INVENTION

Field of the Invention

The present invention relates to inspection apparatuses for inspecting targets using a plurality of lights, which have different polarization states from each other.

Priority is claimed on Japanese Patent Application No. 2014-113950, filed on Jun. 2, 2014, the contents of which are incorporated herein by reference.

Description of Related Art

Inspection apparatuses using polarized lights are for irradiating an inspection target with a light, which has a specific polarization state (a linear polarization state or a circular polarization state), receiving a plurality of reflected lights (or, a plurality of transmitted rights), which are obtained from the inspection target and have different polarization states from each other, and inspecting the target. Such inspection apparatuses are used for inspecting surface defects of products or internal defects of products (dust, scratch, non-uniformity, and the like).

Research and development of various devices using organic materials has been actively performed in light of the diversity of function and configuration of the organic materials. The inspection apparatuses are often used for inspecting the quality of thin films (organic thin films) using such organic materials. For example, the inspection apparatuses are often used for inspecting polarizing films, which are used for organic thin-film photovoltaic cells, organic Electro Luminescence (EL) displays, liquid crystal displays, and the like, Radio Frequency IDentification (RFID) tags using organic semiconductors, and the like.

Japanese Unexamined Patent Application, First Publication No. H09-178666 (hereinafter, referred to as "PTL1") and Japanese Unexamined Patent Application, First Publication No. 2007-322316 (hereinafter, referred to as "PTL2") disclose examples of inspection apparatuses using polarized lights in the related art. In particular, the PTL1 discloses an inspection apparatus using polarized lights that splits a reflected light from a surface of a steel plate, which is an inspection target, into three different types of polarized lights using a beam splitter, measures the polarized lights using a linear array camera, calculates the ellipse-parameters of the reflected light, and judges the type and grade of the surface defects of the inspection target. The PTL2 discloses an inspection apparatus using polarized lights that selects a plurality of liner polarized lights, which is the most suitable for the inspection, and irradiates an inspection target with the liner polarized lights, so as to overcome the situation where the change of the reflection plane caused by the movement of the inspection target makes the detection of defects difficult.

It is often the case that the above-stated thin film such as an organic thin film is manufactured by a continuous manufacturing process referred to as a "roll-to-toll process". The above-stated continuous manufacturing process referred to as the "roll-to-toll process" continuously applies an organic material and the like while drawing a rolled film to form an organic thin film, then, rolls the film again, on which the organic thin film is formed. The inspection of the organic thin film manufactured by such a process is generally performed while the organic thin film to be inspected is being moved.

It seems that the inspection apparatus disclosed in the PTL 1 or the PTL 2 allows the inspection of the target while the inspection target is being moved. The inspection apparatus disclosed in the PTL 1 is suitable for inspection of surface defects of an inspection target, which has high surface reflectance, such as a steel plate, but the inspection apparatus is not suitable for inspection of the quality of, for example, an organic thin film (inspection whether an orientation of a molecular material is appropriate). This holds true for the PTL 2.

SUMMARY OF THE INVENTION

One aspect of the present invention provides inspection apparatuses using polarized lights, which allow accurate inspection of the quality of films included in inspection targets even while the inspection targets are being moved.

An inspection apparatus using polarized lights according to one aspect of the present invention may include an irradiator configured to irradiate an inspection target with a first plurality of lights. The first plurality of lights may have different polarization states and different wavelengths from each other. The inspection apparatus may further include a light receiver configured to perform a wavelength demultiplexing of a second plurality of lights obtained from the inspection target to generate a third plurality of lights, to separately receive the third plurality of lights, and to output at least one light-receiving signal associated with the third plurality of lights and a processor configured to calculate at least one of an ellipse azimuth, a degree of polarization, and a polarization component intensity using the light-receiving signal and to determine whether the inspection target is defective or non-defective.

In the inspection apparatus, the irradiator may include a plurality of light sources and a multiplexer. Each of the light sources may be configured to emit a light having a different polarization state and different wavelength from those of another light sources. The multiplexer may be configured to multiplex the lights emitted from the light sources and to irradiate one-dimensional or two-dimensional inspection region defined on the inspection target with the multiplexed light.

In the inspection apparatus, the light receiver may include a demultiplexer configured to perform the wavelength demultiplexing of the second plurality of lights to generate the third plurality of lights and at least one imager configured to separately receive the third plurality of lights.

In the inspection apparatus, the light receiver may include a plurality of imagers. Each of the imagers may be disposed for a respective light of the third plurality of lights.

In the inspection apparatus, the light receiver may include single imager configured to separately receive the third plurality of lights. The imager may include an imaging plane. The third plurality of lights may be incident on different regions of the imaging plane from each other.

In the inspection apparatus, the processor may be configured to calculate a distribution of at least one of the ellipse azimuth, the degree of polarization, and the polarization component intensity in a plane of the inspection target.

In the inspection apparatus, the processor may be configured to determine whether the inspection target is defective or non-defective based on one of a first determination result whether the ellipse azimuth is greater than a predetermined first threshold value, a second determination result whether the degree of polarization is greater than a predetermined second threshold value, and a third determination result whether the polarization component intensity is greater than a predetermined third threshold value.

In the inspection apparatus, the light receiver may be configured to receive reflected lights of the first plurality of lights or transmitted lights of the first plurality of lights.

In the inspection apparatus, the multiplexer may be configured to multiplex the lights emitted from the light sources while maintaining a polarized wave state of each light.

In the inspection apparatus, the irradiator may be configured to irradiate the inspection target with the first plurality of lights. Each of the first plurality of lights may have a linear polarization state. The light receiver may be configured to perform the wavelength demultiplexing of a second plurality of lights to generate the third plurality of lights and to separately receive the third plurality of lights. Each of the second plurality of lights may have an ellipse polarization state.

In the inspection apparatus, the imager may be configured to output the light-receiving signal associated with an image indicating a luminance distribution of the third plurality of lights.

In the inspection apparatus, the processor may be configured to process the light-receiving signal to calculate a luminance data indicating a luminance for each pixel of the imager, and calculate at least one of the ellipse azimuth, the degree of polarization, and the polarization component intensity using the luminance data.

In the inspection apparatus, each of the imagers may be configured to output the light-receiving signal associated with each of the third plurality of lights.

In the inspection apparatus, the imager may be configured to output the light-receiving signal associated with the third plurality of lights.

In the inspection apparatus, the processor may be configured to divide the light-receiving signal into a plurality of image signals. Each of the image signals may indicate a respective image of the third plurality of lights.

The inspection apparatus according to one aspect of the present invention is not configured to demultiplex and receive one light, but is configured to irradiate an inspection target with a plurality of lights, which have different polarization states from each other and different wavelengths from each other, to perform a wavelength demultiplexing of a light obtained from the inspection target, and separately receive the demultiplexed lights. Therefore, the measurement of the light obtained from the inspection target can be executed without decreasing the light-receiving signal level. In addition, since an analyzer is not disposed in front of an imager, the incident angle dependence can be reduced and the quality of a film included in the inspection target can be inspected accurately in the polarization measurement process. In addition, since there is no movable element in the apparatus, the inspection of the target can be executed rapidly even while the inspection target is being moved.

DETAILED DESCRIPTION OF THE INVENTION

Hereinafter, inspection apparatuses using polarized lights according to several embodiments of the present invention will be described with reference to the drawings.

First Embodiment

Figure 1:
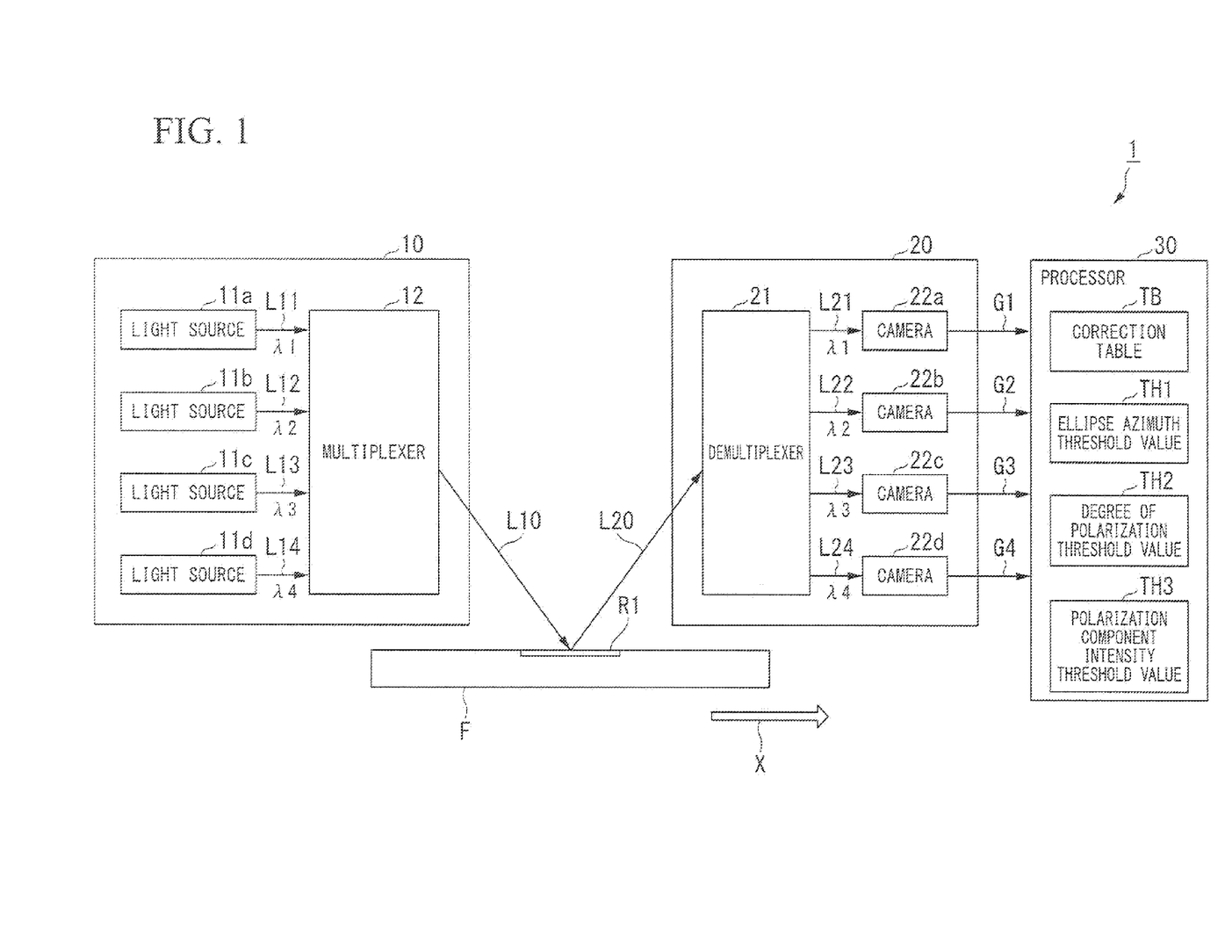
FIG. 1 is a block diagram showing main elements included in an inspection apparatus using polarized lights according to a first embodiment of the present invention.

FIG. 1 is a block diagram showing main elements included in an inspection apparatus using polarized lights according to the first embodiment of the present invention. As shown in FIG. 1, an inspection apparatus 1 using polarized lights according to the first embodiment includes an irradiator 10, a light receiver 20, and a processor 30 and inspects the quality of a film included in an inspection target F in transfer state in a transfer direction X. In particular, the inspection apparatus 1 is a reflection-type inspection apparatus that irradiates the inspection target F with an illumination light L10 including a plurality of lights L11 to L14, which have different polarization states from each other and different wavelengths from each other, performs a wavelength demultiplexing of a reflected light L20 obtained from the inspection target F to generate lights L21 to L24, separately receives the lights L21 to L24, and inspects the quality of the film included in the inspection target F.

The inspection target F may include, for example, organic thin films. The organic thin film may include polarizing films used for organic thin film photovoltaic cells, organic EL displays, liquid crystal displays, and the like, and films used for devices such as RFID tags using organic semiconductors and films included in the devices. Hereinafter, the direction, which is perpendicular to the transfer direction X of the inspection target F and is included in the plane of the inspection target F, is referred to as the "width direction Y".

The irradiator 10 includes a plurality of light sources 11a to 11d and a multiplexer 12 and is disposed above a first surface of the inspection target F. The irradiator 10 irradiates an inspection region R1 defined on the inspection target F with the illumination light L10 including the plurality of lights L11 to L14, which have different polarization states from each other and different wavelengths from each other. The inspection region R1 defined on the inspection target F is a rectangular region (two-dimensional region) having a first length in the transfer direction X and a second length in the width direction Y, each of which is, for example, in the range from about several centimeters to about several tens centimeters. The size of the inspection region R1 is appropriately set based on the size of the inspection target F.

The light sources 11a to 11d respectively emit the lights L11 to L14, which have different polarization states from each other and different wavelengths from each other. In particular, the light source 11a emits a linear polarized light L11 where the wavelength is $\lambda 1$ and the vibration direction of the electric field is 0°. The light source 11b emits a linear polarized light L12 where the wavelength is λ2 and the vibration direction of the electric field is 45°. The light source 11c emits a linear polarized light L13 where the wavelength is λ3 and the vibration direction of the electric field is 90°. The light source 11d emits a linear polarized light L14 where the wavelength is λ4 and the vibration direction of the electric field is 135°.

The wavelengths of the lights L11 to L14 respectively emitted by the light sources 11a to 11d are appropriately set based on the optical characteristic and the configuration of the inspection target F. The wavelengths of the lights L11 to L14 may be in a visible region or in a region other than a visible region (for example, an infrared region). Each of the wavelengths of the lights L11 to L14 is required to be set so as to allow the light receiver 20 described below to perform the wavelength demultiplexing. In the first embodiment, the vibration direction of the electric field of each of the lights L11 to L14 is represented by an angle in a plane perpendicular to the moving direction of the lights L11 to L14 and a direction perpendicular to the incident plane of the inspection target F, into which the lights L11 to L14 enter, is defined as 0°. In other words, the direction perpendicular to the sheet of FIG. 1 is defined as 0°.

The multiplexer 12 includes, for example, a dichroic mirror (or prism) and multiplexes the lights L11 to L14 respectively emitted from the light sources 11a to 11d while maintaining each polarized wave state. The multiplexer 12 irradiates the inspection region R1 defined on the inspection target F with the multiplexed light (illumination light L10).

The light receiver 20 includes a demultiplexer 21 and a plurality of cameras 22a to 22d (imagers). Similarly to the irradiator 10, the light receiver 20 is disposed above the first surface of the inspection target F. The light receiver 20 performs a wavelength demultiplexing of the reflected light L20 obtained from the inspection target F to generate the lights L21 to L24 and separately receives the dispersed lights L21 to L24. The L21 to L24 are respectively obtained from the lights L11 to L14, which are incident on the inspection region R1 defined on the inspection target F and are reflected by the inspection region R1.

Similarly to the multiplexer 12 included in the irradiator 10, the demultiplexer 21 includes, for example, a dichroic mirror (or prism) and performs a wavelength demultiplexing of the reflected light L20 to generate the lights L21 to L24. The polarization states of the lights L21 to L24 obtained by the wavelength demultiplexing may be or may not be maintained equal to the states before the wavelength demultiplexing.

The cameras 22a to 22d are provided associated with the plurality of lights L21 to L24, which are obtained by the wavelength demultiplexing using the demultiplexer 21. The cameras 22a to 22d respectively images (receives) the lights L21 to L24, which are obtained by the wavelength demultiplexing using the demultiplexer 21. Each of the cameras 22a to 22d includes an imaging device such as a Charge Coupled Device (CCD) and a Complementary Metal Oxide Semiconductor (CMOS). The cameras 22a to 22d respectively output image signals G1 to G4 (light reception signals) according to the imaged images (the images indicating the luminance distributions of the lights L21 to L24 obtained from the inspection region R1).

The processor 30 calculates an ellipse azimuth, a degree of polarization, and a polarization component intensity using the plurality of image signals G1 to G4 output from the light receiver 20 and determines whether the inspection target F is defective or non-defective. In particular, the processor 30 executes a processing for processing the image signals G1 to G4 to calculate luminance data I1 to I4 for each pixel (each pixel of the cameras 22a to 22d), a processing for calculating Stokes parameters S (S0 to S2) for each pixel based on the luminance data I1 to I4, and a processing for calculating an ellipse azimuth Ψ, a degree of polarization DoP, and a polarization component intensity IP for each pixel using the Stokes parameters S (S0 to S2). In other words, the processor 30 executes a processing for calculating the two-dimensional distribution of the ellipse azimuth Ψ, the degree of polarization DoP, and the polarization component intensity IP in the inspection region R1 defined on the inspection target F.

The above-stated luminance data I1 indicates the luminance of the light L21, which is obtained by irradiating the inspection target F with the light L11, for each pixel. The light L11 is a linear polarized light where the vibration direction of the electric field is 0°. The above-stated luminance data I2 indicates the luminance of the light L22, which is obtained by irradiating the inspection target F with the light L12, for each pixel. The light L12 is a linear polarized light where the vibration direction of the electric field is 45°. The above-stated luminance data I3 indicates the luminance of the light L23, which is obtained by irradiating the inspection target F with the light L13, for each pixel. The light L13 is a linear polarized light where the vibration direction of the electric field is 90°. The above-stated luminance data I4 indicates the luminance of the light L24, which is obtained by irradiating the inspection target F with the light L14, for each pixel. The light L14 is a linear polarized light where the vibration direction of the electric field is 135°.

The processor 30 calculates the Stokes parameters S (S0 to S2) for each pixel using the following equation (1), calculates the degree of polarization DoP for each pixel using the following equation (2), calculates the ellipse azimuth Ψ for each pixel using the following equation (3), and calculates the polarization component intensity IP for each pixel using the following equation (4).

$$S = \begin{pmatrix} S0 \\ S1 \\ S2 \end{pmatrix} = \begin{pmatrix} I1 + I3 \\ I1 - I3 \\ I2 - I4 \end{pmatrix} \quad (1)$$

$$DoP = \frac{2 \cdot \sqrt{S1^2 + S2^2}}{I1 + I2 + I3 + I4} \quad (2)$$

$$\Psi = \frac{1}{2}\tan^{-1}(S2/S1) \quad (3)$$

$$IP = \frac{I1 + I2 + I3 + I4}{4} + \frac{\sqrt{S1^2 + S2^2}}{2} \cdot \cos(2(\theta - \Psi)) \quad (4)$$

As shown in FIG. 1, the processor 30 includes a correction table TB. The correction table TB stores correction amount for correcting the variation in the intensity of each of the lights L11 to L14 respectively emitted from the light sources 11a to 11d, the variation in the characteristic of each of the cameras 22a to 22d (light-receiving characteristic), and the variation in the reflectance of the surface of the inspection target F according to the wavelengths of the lights L11 to L14. The processor 30 corrects each variation described above using the correction amount stored in the correction table TB and then calculates the Stokes parameters S (S0 to S2), the degree of polarization DoP, the ellipse azimuth Ψ, and the polarization component intensity IP described above.

The processor 30 further includes an ellipse azimuth threshold value TH1 (first threshold value), a degree of polarization threshold value TH2 (second threshold value), and a polarization component intensity threshold value TH3 (third threshold value). The ellipse azimuth threshold value TH1 is defined for the ellipse azimuth Ψ calculated using the above-stated equation (3) so as to determine whether the inspection target F is defective or non-defective. The degree of polarization threshold value TH2 is defined for the degree of polarization DoP calculated using the above-stated equation (2) so as to determine whether the inspection target F is defective or non-defective. The polarization component intensity threshold value TH3 is defined for the polarization component intensity IP calculated using the above-stated equation (4) so as to determine whether the inspection target F is defective or non-defective.

If the ellipse azimuth Ψ calculated using the above-stated equation (3) is greater than the ellipse azimuth threshold value TH1, the degree of polarization DoP calculated using the above-stated equation (2) is greater than the degree of polarization threshold value TH2, and the polarization component intensity IP calculated using the above-stated equation (4) is greater than the polarization component intensity threshold value TH3, then the processor 30 determines that the inspection target F is defective. Alternatively, if any one (or any two) of the ellipse azimuth Ψ calculated using the above-stated equation (3), the degree of polarization DoP calculated using the above-stated equation (2), and the polarization component intensity IP calculated using the above-stated equation (4) is greater than the threshold value, then the processor 30 may determine that the inspection target F is defective.

Next, the operation of the inspection apparatus 1 having the above-stated configuration will be described. When the inspection is started, an unshown controller controls the irradiator 10 so that the light sources 11a to 11d emit the lights L11 to L14, respectively. The lights L11 to L14 respectively emitted from the light sources 11a to 11d are incident on the multiplexer 12 and are multiplexed while maintaining each polarized wave state. The multiplexed light (illumination light L10) is emitted from the multiplexer 12 and is incident on the inspection region R1 defined on the inspection target F.

Figure 2:
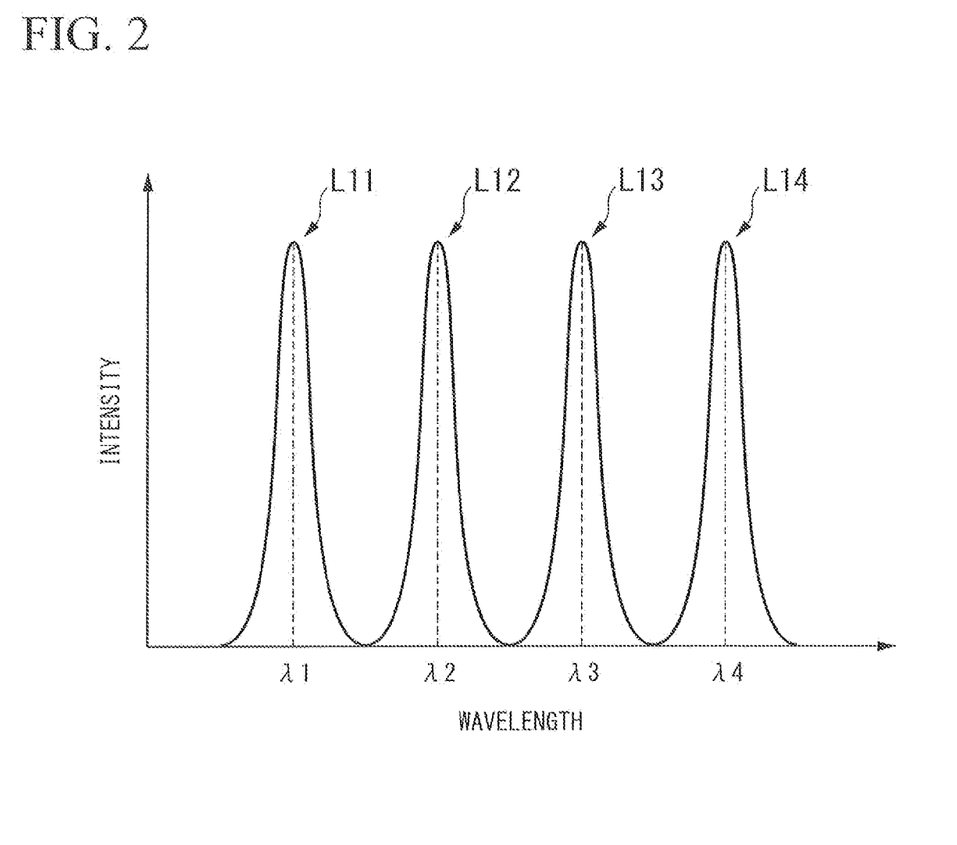
FIG. 2 is a diagram showing an example of a spectrum of an illumination light to be incident on an inspection target.

FIG. 2 is a diagram showing an example of a spectrum of an illumination light to be incident on the inspection target. Since the illumination light L10 to be incident on the inspection target F is obtained by multiplexing the lights L11 to L14 respectively emitted from the light sources 11a to 11d, the spectrum of the illumination light L10 has a waveform including peak wavelengths λ1 to λ4 as shown in FIG. 2. The wavelengths λ1 to λ4 are aligned at a predetermined interval, for example, an interval of about 200 nm.

Figure 3:
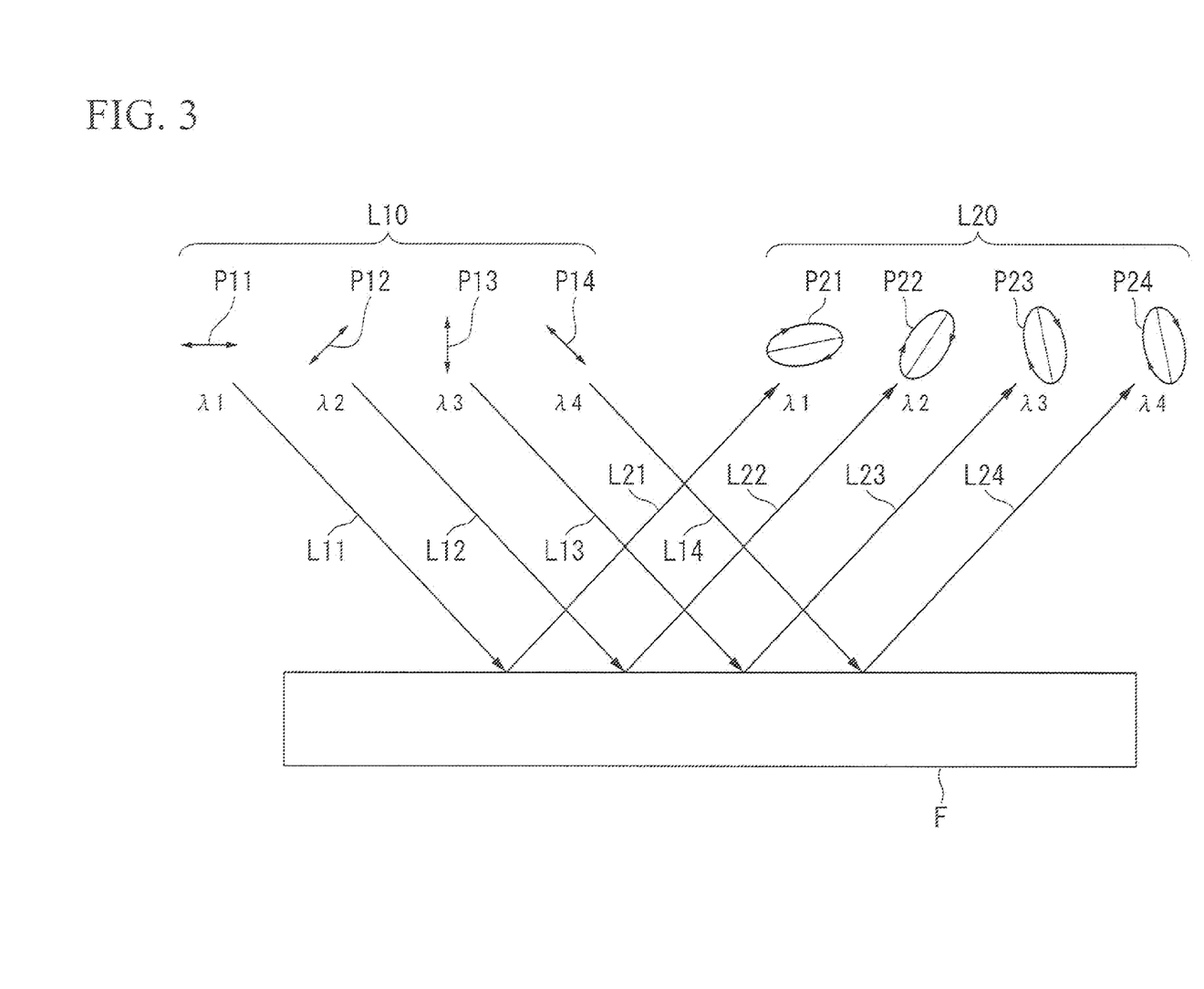
FIG. 3 is a diagram showing an example of polarization states of illumination lights to be incident on the inspection target and polarization states of reflected lights obtained from the inspection target.

FIG. 3 is a diagram showing an example of polarization states of illumination lights to be incident on the inspection target and polarization states of reflected lights obtained from the inspection target. FIG. 3 shows the optical paths of the lights L11 to L14 included in the illumination light L10, the polarization states P11 to P14 of the lights L11 to L14, the optical paths of the lights L21 to L24 included in the reflected light L20 and the polarization states P21 to P24 of the lights L21 to L24.

The polarization states P11 to P14 shown in FIG. 3 are represented along the direction in which the lights L11 to L14 advance, and the polarization states P21 to P24 are represented along the direction in which the lights L21 to L24 advance. The lights L11 to L14 included in the illumination light L10 advance along the same optical path as each other and the lights L21 to L24 included in the reflected light L20 advance along the same optical path as each other. In FIG. 3, in order to facilitate the understanding, the optical paths of the lights L11 to L14 are shown separately from each other and the optical paths of the lights L21 to L24 are shown separately from each other.

As shown in FIG. 3, each of the polarization states P11 to P14 of the lights L11 to L14 included in the illumination light L10 is a linear polarization state. In particular, the light L11 in the polarization state P11 is a linear polarized light where the vibration direction of the electric field is 0° and the light L12 in the polarization state P12 is a linear polarized light where the vibration direction of the electric field is 45°. The light L13 in the polarization state P13 is a linear polarized light where the vibration direction of the electric field is 90° and the light L14 in the polarization state P14 is a linear polarized light where the vibration direction of the electric field is 135°. In other words, the lights L11 to L14 are incident on the inspection target F while the polarization states at the time when the lights L11 to L14 are respectively emitted from the light sources 11a to 11d are maintained.

On the other hand, each of the polarization states P21 to P24 of the lights L21 to L24 included in the reflected light L20 is an elliptically polarization state. This is because the lights L11 to L14 included in the illumination light L10 are incident on the inspection target F, thereby, each polarization state is changed. The changing of the polarization state of each of the lights L21 to L24 included in the reflected light L20 is depending on the optical characteristic, the configuration, the quality of the film of the inspection target F, and the like.

The reflected light L20 reflected from the inspection region R1 defined on the inspection target F is incident on the light receiver 20 and is subjected to the wavelength demultiplexing using using the demultiplexer 21 included in the light receiver 20 to be divided into the lights L21 to L24. The demultiplexed lights L21 to L24 are incident on the cameras 22a to 22d, respectively and are separately imaged. The cameras 22a to 22d inputs the image signals G1 to G4 according to the imaged images (the images indicating the luminance distributions of the lights L21 to L24 obtained from the inspection region R1) into the processor 30.

When the processor 30 receives the image signals G1 to G4, the processor 30 firstly processes the image signals G1 to G4 to calculate the luminance data I1 to I4, each of which indicates the luminance of each pixel (pixels included in each of the cameras 22a to 22d). In this processing, each variation (the variation in the intensity of each of the lights L11 to L14 emitted from the light sources 11a to 11d, the variation in the characteristic of each of the cameras 22a to 22d (light-receiving characteristic), and the variation in the reflectance of the surface of the inspection target F according to the wavelengths of the lights L11 to L14) is corrected using the correction amount stored in the correction table TB.

Next, the processor 30 calculates the Stokes parameters S (S0 to S2) from the luminance data I1 to I4 and then calculates the ellipse azimuth Ψ, the degree of polarization DoP, and the polarization component intensity IP for each pixel using the Stokes parameters S (S0 to S2). After the above-stated processing is finished, the processor 30 compares the calculated ellipse azimuth Ψ, the calculated degree of polarization DoP, and the calculated polarization component intensity IP with the ellipse azimuth threshold value TH1, the degree of polarization threshold value TH2, and the polarization component intensity threshold value TH3, respectively, and determines whether the inspection target F is defective or non-defective.

For example, if the calculated ellipse azimuth is greater than the ellipse azimuth threshold value TH1, the calculated degree of polarization DoP is greater than the degree of polarization threshold value TH2, and the calculated polarization component intensity IP is greater than the polarization component intensity threshold value TH3, then the processor 30 determines that the inspection target F is defective. On the other hand, if any one of the calculated ellipse azimuth Ψ, the calculated degree of polarization DoP, and the calculated polarization component intensity IP is not greater than the threshold value, then the processor 30 determines that the inspection target F is non-defective.

Such a result determined by the processor 30 is displayed on, for example, a display (not-shown) provided in the processor 30 or is reported via sound or the like. Alternatively, the result is transmitted to a host device (not-shown). The above-stated operations are repeated under the condition where the inspection target F is transferred in the transfer direction X, thereby, the quality of the film included in the inspection target F in the transfer direction X is continuously inspected in the range of the width of the inspection region R1 in the width direction Y.

As described above, in the first embodiment, the illumination light L10 including the plurality of lights L11 to L14, which have different polarization states from each other and different wavelengths from each other, is incident on the inspection region R1 defined on the inspection target F, the reflected light L20 obtained from the inspection target F is subjected to the wavelength demultiplexing to be divided into the lights L21 to L24 and the lights L21 to L24 are separately imaged, the ellipse azimuth Ψ, the degree of polarization DoP, and the polarization component intensity IP are calculated using the image signals G1 to G4 obtained by the above-stated imaging, and whether the inspection target F is defective or non-defective is determined. Therefore, even while the inspection target F is being moved, the quality of the film included in the inspection target F can be inspected accurately. Since, in the first embodiment, the image of the rectangular inspection region R1 defined on the inspection target F is imaged by the cameras 22a to 22d, the quality of the film included in the inspection target F can be inspected even while the inspection target F is not being moved.

Second Embodiment

Figure 4:
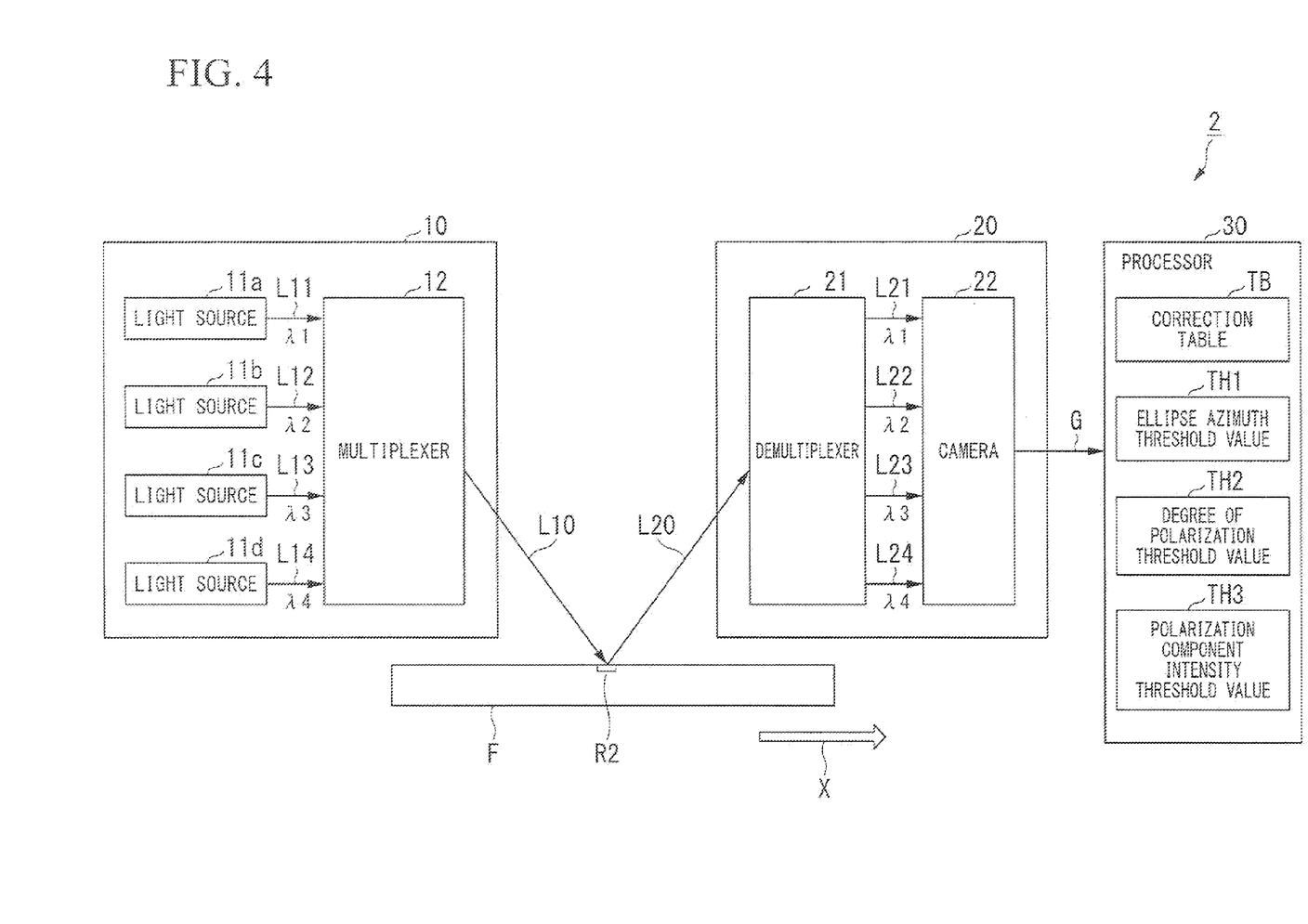
FIG. 4 is a block diagram showing main elements included in an inspection apparatus using polarized lights according to a second embodiment of the present invention.

FIG. 4 is a block diagram showing main elements included in an inspection apparatus using polarized lights according to the second embodiment of the present invention. In FIG. 4, blocks that correspond to those in FIG. 1 are assigned the same reference numerals. An inspection apparatus 2 using polarized lights shown in FIG. 4 is different from the inspection apparatus 1 shown in FIG. 1 in that a line-shaped inspection region R2 (one-dimensional region) extending in the width direction Y is defined on the inspection target F and single camera 22, which is similarly to each of the cameras 22a to 22d shown in FIG. 1, is provided instead of the cameras 22a to 22d.

In the inspection apparatus 1 shown in FIG. 1, the rectangular inspection region R1 is defined on the inspection target F, the lights L21 to L24, which are included in the reflected light L20 reflected from the inspection region R1, are imaged by the cameras 22a to 22d, respectively. However, if, for example, the inspection target F is manufactured by a continuous manufacture process referred to as a roll-to-roll process, then the inspection target F is transferred in the transfer direction X at a constant rate. Therefore, it is not always necessary to image the image of the rectangular inspection region R1 using the cameras 22a to 22d. In the inspection apparatus 2 according to the second embodiment, the line-shaped inspection region R2 is defined on the inspection target F, and the number of cameras is reduced so as to simplify the configuration. Thereby, the cost is reduced and the problem of alignment caused by the mis-registration among the cameras is resolved.

In the second embodiment, since the line-shaped inspection region R2 is defined on the inspection target F, a multiplexer 12 included in an irradiator 10 is configured to irradiate the inspection region R2 with a line-shaped illumination light L10. In addition, in the second embodiment, since it is necessary to image lights L21 to L24 included in a line-shaped reflected light L20 by the single camera 22, a demultiplexer 21 and the camera 22, which are included in a light receiver 20, are configured as shown in FIG. 5.

Figure 5:
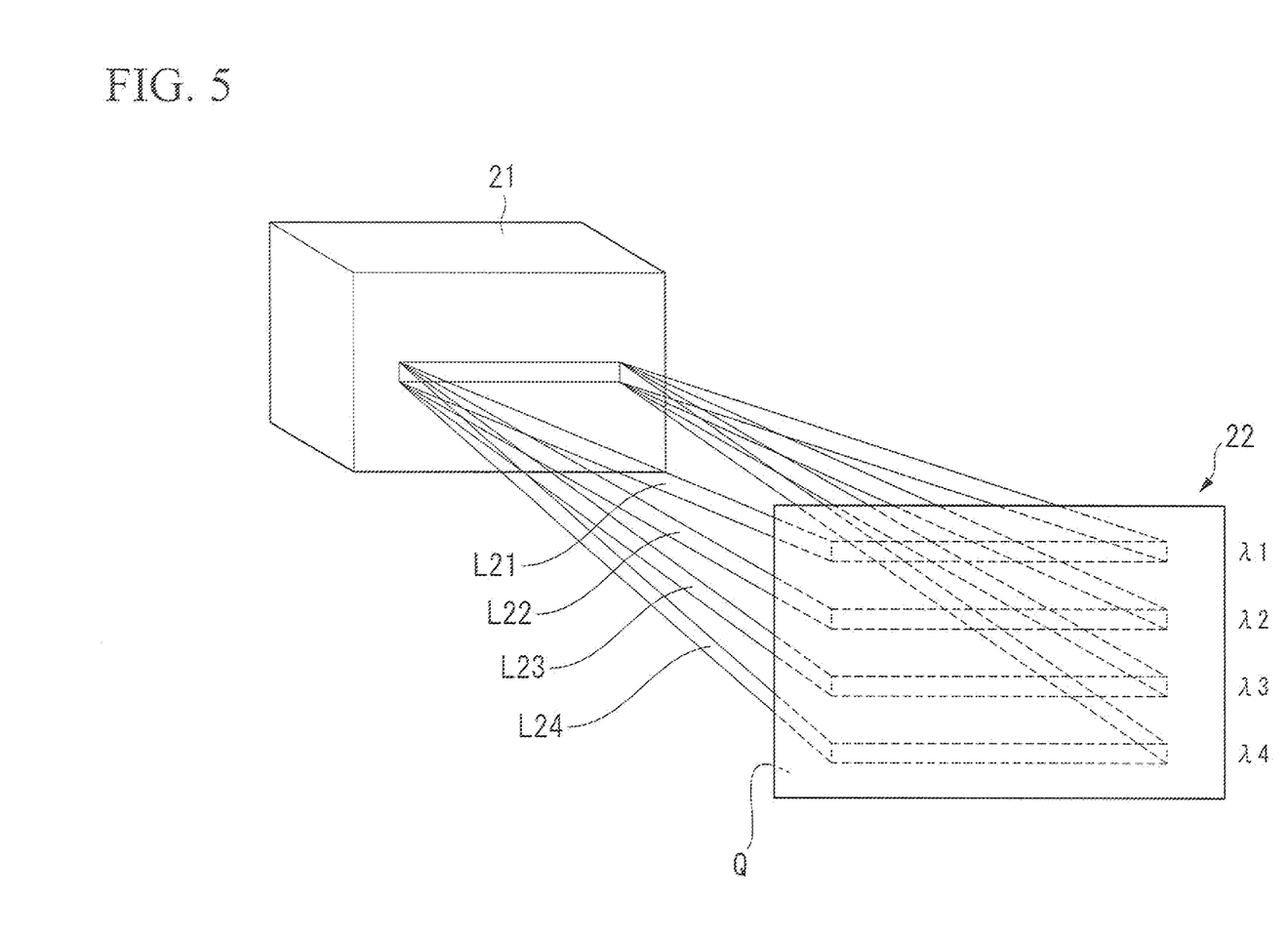
FIG. 5 is a diagram showing a correlation between a demultiplexer and a camera according to the second embodiment of the present invention.

FIG. 5 is a diagram showing a correlation between a demultiplexer and a camera according to the second embodiment of the present invention. As shown in FIG. 5, the demultiplexer 21 and the camera 22 are configured so that the lights L21 to L24 emitted from the demultiplexer 21 are incident on an imaging plane Q of the camera 22 under the condition where the lights L21 to L24 are not superimposed on each other and are spacially separated from each other. In other words, the lights L21 to L24 emitted from the demultiplexer 21 are incident on different regions in the imaging plane Q from each other and the camera 22 separately image (receive) the lights L21 to L24. If the intervals among the lights L21 to L24 to be incident on the imaging plane Q are narrow, then an image G output from the camera 22 will be an image reflected by the interferences among the lights L21 to L24. Therefore, the interval between the lights L21 to L24 to be incident on the imaging plane Q is set to have a spacial allowance (for example, the interval equal to about several tens to about one hundred pixels of the camera 22).

Figure 6:
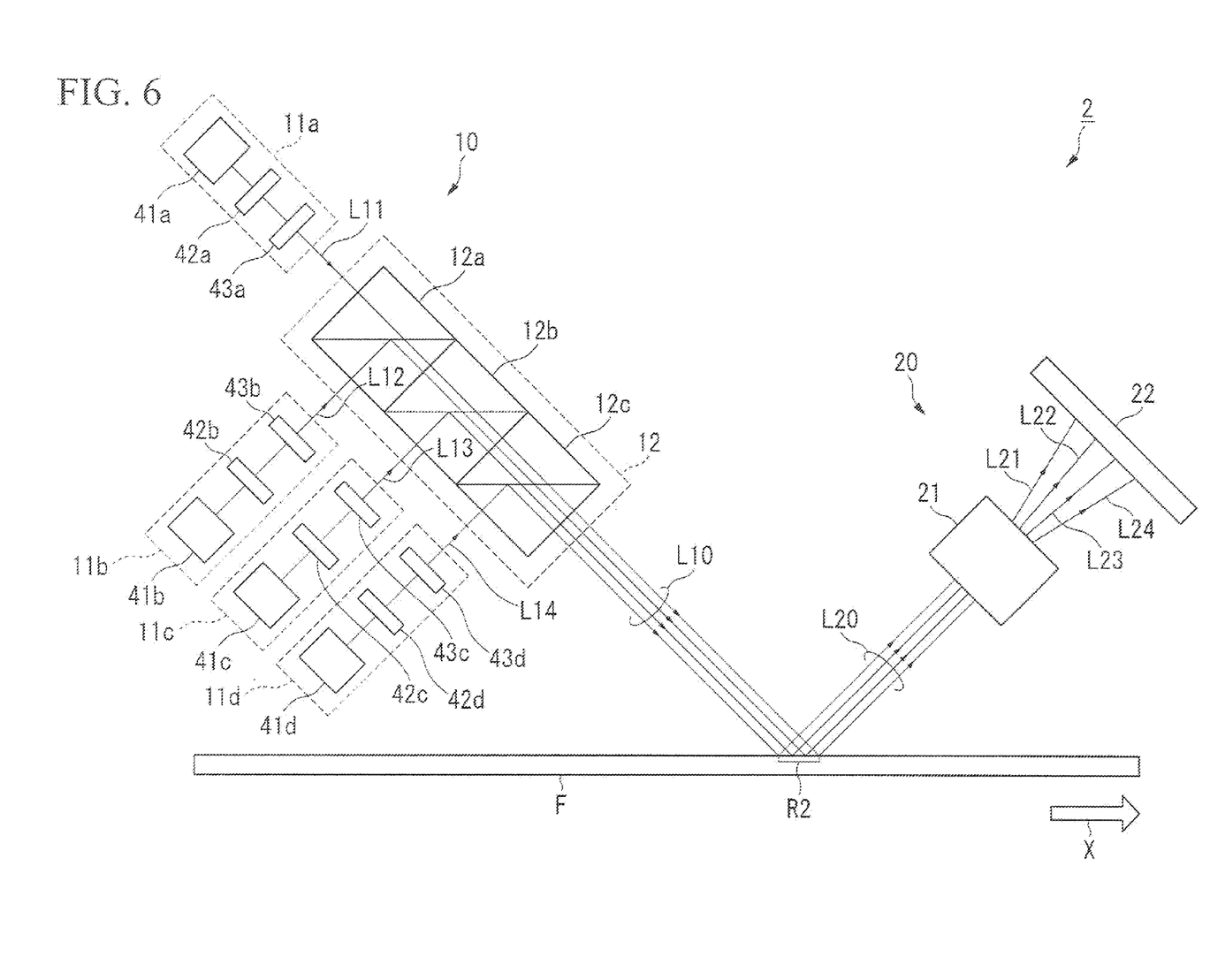
FIG. 6 is a diagram showing a specific configuration example of the inspection apparatus according to the second embodiment of the present invention.

Next, a specific configuration of the inspection apparatus according to the second embodiment of the present invention will be described. FIG. 6 is a diagram showing a specific configuration example of the inspection apparatus according to the second embodiment of the present invention. In FIG. 6, blocks that correspond to those in FIG. 4 are assigned the same reference numerals. Similarly to FIG. 3, the optical paths of the lights L11 to L14 included in the illumination light L10 are shown separately from each other and the optical paths of the lights L21 to L24 included in the reflected light L20 are shown separately from each other.

As shown in FIG. 6, each of light sources 11a to 11d included in the irradiator 10 includes a light, a polarizer, and a lens. In particular, the light source 11a includes a light 41a, a polarizer 42a and a lens 43a, the light source 11b includes a light 41b, a polarizer 42b, and a lens 43b. Similarly, the light source 11c includes a light 41c, a polarizer 42c, and a lens 43c and the light source 11d includes a light 41d, a polarizer 42d, and a lens 43d.

Each of the lights 41a to 41d includes, for example, a Light Emitting Diode (LED), a Laser Diode (LD), or the like. The light 41a emits a light having a wavelength λ1, the light 41b emits a light having a wavelength λ2, the light 41c emits a light having a wavelength λ3, and the light 41d emits a light having a wavelength λ4. The polarization state of each of the lights emitted from the lights 41a to 41d may be one of a circular polarization state, an elliptic polarization state, and a random state. The polarizer 42a changes the polarization state of the light, which is emitted from the light 41a and has the wavelength λ1, to a linear polarization state where the vibration direction of the electric field is 0°. The polarizer 42b changes the polarization state of the light, which is emitted from the light 41b and has the wavelength λ2, to a linear polarization state where the vibration direction of the electric field is 45°. The polarizer 42c changes the polarization state of the light, which is emitted from the light 41c and has the wavelength λ3, to a linear polarization state where the vibration direction of the electric field is 90°. The polarizer 42d changes the polarization state of the light, which is emitted from the light 41d and has the wavelength λ4, to a linear polarization state where the vibration direction of the electric field is 135°. The lens 43a is provided so as to focus the light emitted from the polarizer 42a on the line-shaped inspection region R2 defined on the inspection target F, the lens 43b is provided so as to focus the light emitted from the polarizer 42b on the line-shaped inspection region R2, the lens 43c is provided so as to focus the light emitted from the polarizer 42c on the line-shaped inspection region R2, and the lens 43d is provided so as to focus the light emitted from the polarizer 42d on the line-shaped inspection region R2.

The multiplexer 12 included in the irradiator 10 includes three dichroic mirrors 12a to 12c. The dichroic mirror 12a has a characteristic to transmit a light, which has a wavelength λ1, and to reflect a light, which has a wavelength λ2. The dichroic mirror 12b has a characteristic to transmit a light, which has a wavelength λ1 or λ2, and to reflect a light, which has a wavelength λ3. The dichroic mirror 12c has a characteristic to transmit a light, which has one of wavelengths λ1, λ2, and λ3, and to reflect a light, which has a wavelength λ4. The dichroic mirrors 12a to 12c are sequentially arranged in a row along the optical path of the illumination light L10. The dichroic mirrors 12a to 12c multiplex the lights L11 to L14 respectively emitted from the light sources 11a to 11d while maintaining each polarized wave state.

Figure 7:
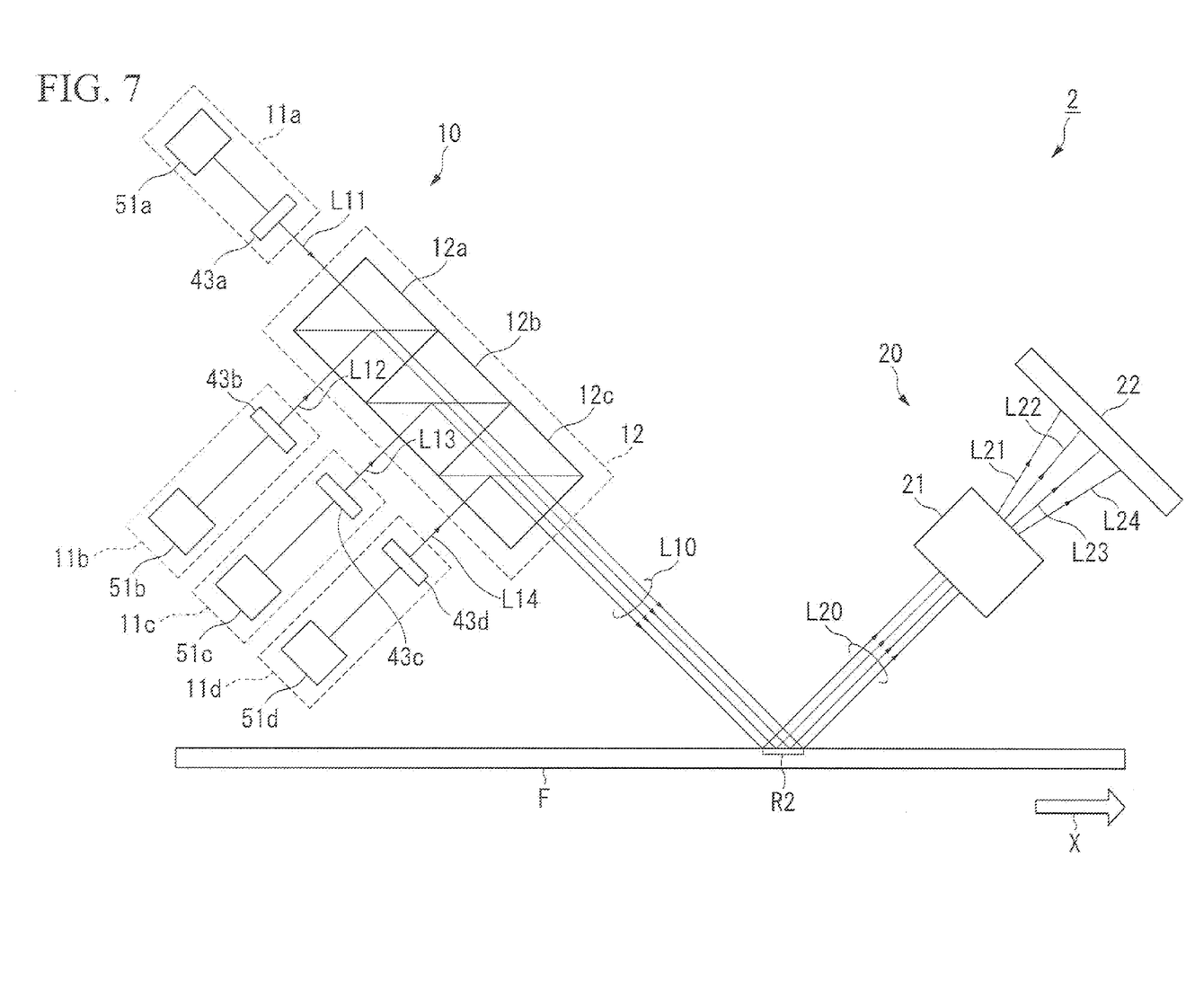
FIG. 7 is a diagram showing another specific configuration example of the inspection apparatus according to the second embodiment of the present invention.

FIG. 7 is a diagram showing another specific configuration example of the inspection apparatus according to the second embodiment of the present invention. An inspection apparatus 2 using polarized lights shown in FIG. 7 has a configuration where the light sources 11a to 11d provided in the inspection apparatus 2 shown in FIG. 6 are changed. In particular, in FIG. 7, the polarizers 42a to 42d provided in the light sources 11a to 11d shown in FIG. 6 are omitted, and lights 51a to 51d are provided instead of the lights 41a to 41d.

Each of the lights 51a to 51d includes an LD for emitting a laser where the polarization state is a linear polarization state. In particular, the light 51a emits a linear polarized light where the wavelength is λ1 and the vibration direction of the electric field is 0° and the light 51b emits a linear polarized light where the wavelength is λ2 and the vibration direction of the electric field is 45°. The light 51c emits a linear polarized light where the wavelength is λ3 and the vibration direction of the electric field is 90° and the light 51d emits a linear polarized light where the wavelength is λ4 and the vibration direction of the electric field is 135°. In the inspection apparatus 2 shown in FIG. 7, the polarizers 42a to 42d can be omitted. Therefore, compared to the inspection apparatus 2 shown in FIG. 6, the inspection apparatus 2 shown in FIG. 7 has the simplified configuration.

Next, the operation of the inspection apparatus 2 having the above-stated configuration will be described. Since the operation of the inspection apparatus 2 is basically similar to that of the inspection apparatus 1 shown in FIG. 1, hereinafter, the description of the operation is simplified. When the inspection is started, an unshown controller controls the irradiator 10 so that the light sources 11a to 11d emit the lights L11 to L14, respectively. The lights L11 to L14 are multiplexed by the multiplexer 12 while maintaining each polarization state. The multiplexed light (illumination light L10) is incident on the line-shaped inspection region R2 defined on the inspection target F.

When the illumination light L10 is incident on the inspection region R2, a line-shaped reflected light L20 is obtained from the inspection target F. The reflected light L20 is subjected to a wavelength demultiplexing using the demultiplexer 21 provided in the light receiver 20 to be divided into line-shaped lights L21 to L24. As shown in FIG. 5, the demultiplexed line-shaped lights L21 to L24 are incident on the imaging plane Q included in the camera 22 and imaged. The camera 22 outputs an image signal G according to the lights L21 to L24.

When a processor 30 receives the image signal G from the camera 22, the processor 30 firstly divides the image signal G into four image signals, which indicate four images of the lights L21 to L24, respectively. The processor 30 processes each divided image signal to calculate luminance data I1 to I4, each of which indicates the luminance for each pixel. Similarly to the first embodiment, a correction processing using the correction amount stored in the correction table TB is executed.

After the above-stated processing is finished, similarly to the first embodiment, the processor 30 calculates Stokes parameters S (S0 to S2) for each pixel from the luminance data I1 to I4 and then calculates an ellipse azimuth Ψ, a degree of polarization DoP, and a polarization component intensity IP for each pixel using the Stokes parameters S (S0 to S2). The processor 30 compares the calculated ellipse azimuth Ψ, the calculated degree of polarization DoP, and the calculated polarization component intensity IP with an ellipse azimuth threshold value TH1, a degree of polarization threshold value TH2, and a polarization component intensity threshold value TH3, respectively, and determines whether the inspection target F is defective or non-defective. The above-stated operations are repeated under the condition where the inspection target F is transferred in the transfer direction X, thereby, the quality of the film included in the inspection target F in the transfer direction X is continuously inspected in the range of the width of the inspection region R2 in the width direction Y.

As described above, in the second embodiment, the illumination light L10 including the plurality of lights L11 to L14, which have different polarization states from each other and different wavelengths from each other, is incident on the line-shaped inspection region R2 defined on the inspection target F, the reflected light L20 obtained from the inspection target F is subjected to the wavelength demultiplexing to be divided into the lights L21 to L24 and the lights L21 to L24 are separately imaged by the single camera 22, the ellipse azimuth Ψ, the degree of polarization DoP, and the polarization component intensity IP are calculated using the image signals G obtained by the above-stated imaging, and whether the inspection target F is defective or non-defective is determined. Therefore, even while the inspection target F is being moved, the quality of the film included in the inspection target F can be inspected accurately.

Although the foregoing has been a description of inspection apparatuses using polarized lights according to several embodiments of the present invention, the present invention is not limited to the embodiments, and can be freely modified within the scope of the present invention. For example, although the above-described embodiment has been described for an example in which the processor 30 calculates the ellipse azimuth Ψ, the degree of polarization DoP, and the polarization component intensity IP and determines whether the inspection target F is defective or non-defective, it is not always necessary to calculate the ellipse azimuth Ψ, the degree of polarization DoP, and the polarization component intensity IP. The processor 30 may calculate any one (or any two) of the ellipse azimuth Ψ, the degree of polarization DoP, and the polarization component intensity IP and determine whether the inspection target F is defective or non-defective.

In addition, the above-stated first embodiment has been described for an example in which the processor 30 calculates the two-dimensional distribution of each of the ellipse azimuth Ψ, the degree of polarization DoP, and the polarization component intensity IP in the inspection region R1 defined on the inspection target F. However, it is not always necessary to calculate the two-dimensional distribution of each of the ellipse azimuth Ψ, the degree of polarization DoP, and the polarization component intensity IP. For example, the processor 30 may calculate only a representative value of each of the ellipse azimuth Ψ, the degree of polarization DoP, and the polarization component intensity IP.

In addition, in the above-stated first embodiment, the lights L21 to L24, which have been demultiplexed by the demultiplexer 21, are imaged by the cameras 22a to 22d, respectively, but the lights L21 to L24 may be imaged by single camera in a similar way to the second embodiment. For example, by providing four shutters (shutters associated with the lights L21 to L24) between the demultiplexer 21 and the camera and making the lights L21 to L24, which have been demultiplexed by the demultiplexer 21, sequentially enter the camera, the lights L21 to L24 can be separately imaged by single camera.

In addition, the above-described embodiment has been described for an example in which the four light sources 11a to 11d are provided in the irradiator 10. However, the number of light sources provided in the irradiator 10 may be equal to two or three or may be equal to or greater than five.

Figure 8:
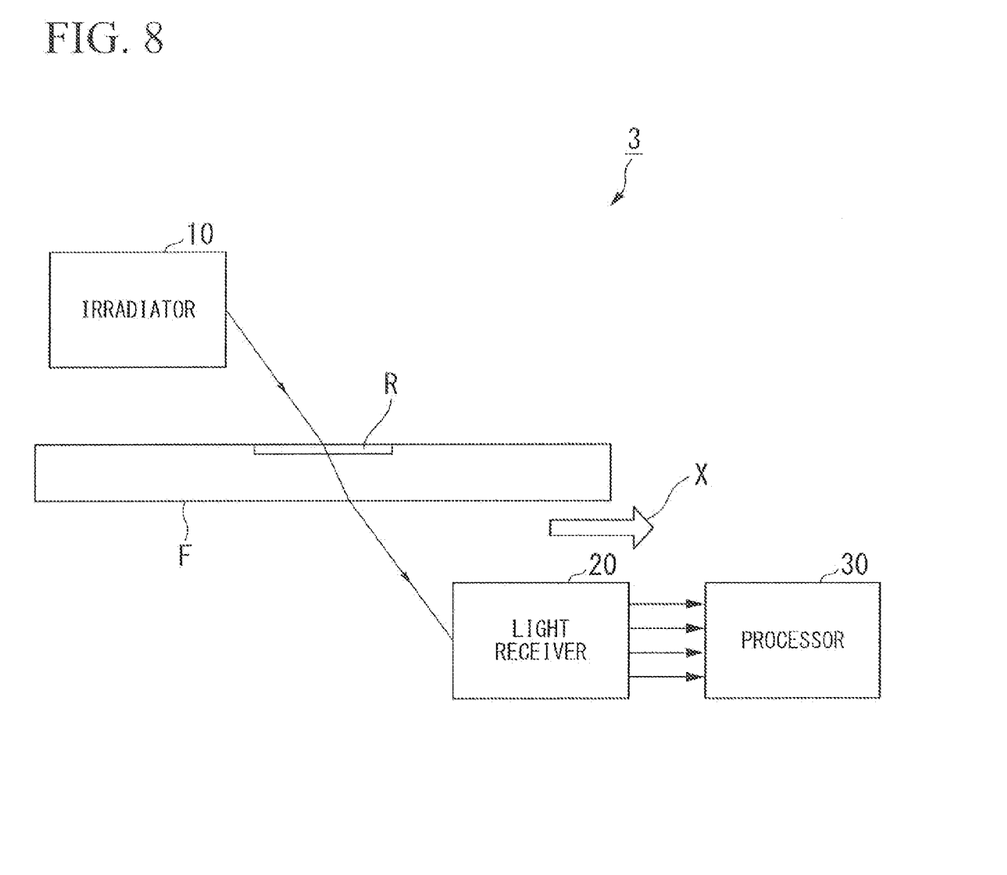
FIG. 8 is a block diagram schematically showing a configuration of a transmission-type inspection apparatus using polarized lights.

Each of the inspection apparatuses 1 and 2 described in the above-stated embodiments is a reflection-type inspection apparatus, which is configured to receive the reflected light L20 obtained from the inspection target F and to inspect the quality of the film included in the inspection target F. However, the present invention is also applicable to a transmission-type inspection apparatus, which is configured to receive a transmitted light transmitting through the inspection target F and to inspect the quality of the film included in the inspection target F. FIG. 8 is a block diagram schematically showing a configuration of a transmission-type inspection apparatus using polarized lights. An inspection apparatus 3 using polarized lights shown in FIG. 8 includes an irradiator 10 disposed above a first surface of an inspection target F (above an inspection region) and a light receiver 20 disposed below a second surface of the inspection target F opposite to the first surface. A processor 30 may be disposed above the first surface of the inspection target F or may be disposed below the second surface of the inspection target F.

In the inspection apparatus 3, an illumination light L10 including a plurality of lights, which have different polarization states from each other and different wavelengths from each other, is incident on an inspection region R defined on the inspection target F, a transmitted light obtained from the inspection target F is subjected to a wavelength demultiplexing and the demultiplexed lights are separately imaged, an ellipse azimuth Ψ, a degree of polarization DoP, and a polarization component intensity IP are calculated using image signals obtained by the above-stated imaging, and whether the inspection target F is defective or non-defective is determined. The inspection region R may be the rectangular inspection region R1 or may be the line-shaped inspection region R2.

In addition, the present invention is also applicable to an inspection apparatus using polarized lights, which combines the above-stated reflection-type inspection apparatus and the above-stated transmission-type inspection apparatus. Such an inspection apparatus includes, for example, an irradiator 10 disposed above a first surface of an inspection target F, a first light receiver 20 disposed above the first surface of the inspection target F, and a second light receiver 20 disposed below a second surface of the inspection target F opposite to the first surface.

What is claimed is:

1. An inspection apparatus using polarized lights comprising:
    an irradiator configured to irradiate an inspection target with a first plurality of lights, the first plurality of lights having different polarization states and different wavelengths from each other;
    a light receiver configured to perform a wavelength demultiplexing of a second plurality of lights obtained from the inspection target to generate a third plurality of lights, to separately receive the third plurality of lights, and to output at least one light-receiving signal associated with the third plurality of lights; and
    a processor configured to calculate at least one of an ellipse azimuth, a degree of polarization, and a polarization component intensity using the light-receiving signal and to determine whether the inspection target is defective or non-defective.

2. The inspection apparatus according to claim 1, wherein the irradiator comprises:
    a plurality of light sources, each of the light sources being configured to emit a light having a different polarization state and different wavelength from those of another light sources; and
    a multiplexer configured to multiplex the lights emitted from the light sources and to irradiate one-dimensional or two-dimensional inspection region defined on the inspection target with the multiplexed light.

3. The inspection apparatus according to claim 2, wherein the light receiver comprises:
    a demultiplexer configured to perform the wavelength demultiplexing of the second plurality of lights to generate the third plurality of lights, and
    at least one imager configured to separately receive the third plurality of lights.

4. The inspection apparatus according to claim 3, wherein the light receiver comprises a plurality of imagers and each of the imagers is disposed for a respective light of the third plurality of lights.

5. The inspection apparatus according to claim 3, wherein the light receiver comprises single imager configured to separately receive the third plurality of lights, the imager includes an imaging plane, and the third plurality of lights are incident on different regions of the imaging plane from each other.

6. The inspection apparatus according to claim 1, wherein the processor is configured to calculate a distribution of at least one of the ellipse azimuth, the degree of polarization, and the polarization component intensity in a plane of the inspection target.

7. The inspection apparatus according to claim 1, wherein the processor is configured to determine whether the inspection target is defective or non-defective based on one of a first determination result whether the ellipse azimuth is greater than a predetermined first threshold value, a second determination result whether the degree of polarization is greater than a predetermined second threshold value, and a third determination result whether the polarization component intensity is greater than a predetermined third threshold value.

8. The inspection apparatus according to claim 1, wherein the light receiver is configured to receive reflected lights of the first plurality of lights or transmitted lights of the first plurality of lights.

9. The inspection apparatus according to claim 2, wherein the multiplexer is configured to multiplex the lights emitted from the light sources while maintaining a polarized wave state of each light.

10. The inspection apparatus according to claim 1, wherein the irradiator is configured to irradiate the inspection target with the first plurality of lights, and each of the first plurality of lights has a linear polarization state, and
the light receiver is configured to perform the wavelength demultiplexing of the second plurality of lights to generate the third plurality of lights and to separately receive the third plurality of lights, and each of the second plurality of lights has an ellipse polarization state.

11. The inspection apparatus according to claim 3, wherein the imager is configured to output the light-receiving signal associated with an image indicating a luminance distribution of the third plurality of lights.

12. The inspection apparatus according to claim 3, wherein the processor is configured to
process the light-receiving signal to calculate a luminance data indicating a luminance for each pixel of the imager, and
calculate at least one of the ellipse azimuth, the degree of polarization, and the polarization component intensity using the luminance data.

13. The inspection apparatus according to claim 4, wherein each of the imagers is configured to output the light-receiving signal associated with each of the third plurality of lights.

14. The inspection apparatus according to claim 5, wherein the imager is configured to output the light-receiving signal associated with the third plurality of lights.

15. The inspection apparatus according to claim 14, wherein the processor is configured to divide the light-receiving signal into a plurality of image signals, and each of the image signals indicates a respective image of the third plurality of lights.

16. The inspection apparatus according to claim 4, wherein the processor is configured to calculate a distribution of at least one of the ellipse azimuth, the degree of polarization, and the polarization component intensity in a plane of the inspection target.

17. The inspection apparatus according to claim 16, wherein the processor is configured to determine whether the inspection target is defective or non-defective based on one of a first determination result whether the ellipse azimuth is greater than a predetermined first threshold value, a second determination result whether the degree of polarization is greater than a predetermined second threshold value, and a third determination result whether the polarization component intensity is greater than a predetermined third threshold value.

18. The inspection apparatus according to claim 17, wherein the light receiver is configured to receive reflected lights of the first plurality of lights or transmitted lights of the first plurality of lights.

19. The inspection apparatus according to claim 5, wherein the processor is configured to calculate a distribution of at least one of the ellipse azimuth, the degree of polarization, and the polarization component intensity in a plane of the inspection target.

20. The inspection apparatus according to claim 19, wherein the processor is configured to determine whether the inspection target is defective or non-defective based on one of a first determination result whether the ellipse azimuth is greater than a predetermined first threshold value, a second determination result whether the degree of polarization is greater than a predetermined second threshold value, and a third determination result whether the polarization component intensity is greater than a predetermined third threshold value.

* * * * *